United States Patent
Jungong et al.

(10) Patent No.: US 10,450,248 B2
(45) Date of Patent: Oct. 22, 2019

(54) METHOD FOR PRODUCING 1,3,3,3-TETRAFLUOROPROPENE (HFO-1234ZE) FROM 1-CHLORO-3,3,3-TRIFLUOROPOPENE (HCFO-1233ZD)

(71) Applicant: Honeywell International Inc., Morris Plains, NJ (US)

(72) Inventors: Christian Jungong, Depew, NY (US); Daniel C. Merkel, Orchard Park, NY (US); Haiyou Wang, Amherst, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 16/177,707

(22) Filed: Nov. 1, 2018

(65) Prior Publication Data

US 2019/0152882 A1     May 23, 2019

Related U.S. Application Data

(60) Provisional application No. 62/589,824, filed on Nov. 22, 2017.

(51) Int. Cl.
| | |
|---|---|
| *C07C 17/37* | (2006.01) |
| *C07C 17/20* | (2006.01) |
| *C07C 17/358* | (2006.01) |
| *C07C 21/18* | (2006.01) |

(52) U.S. Cl.
CPC .............. *C07C 17/20* (2013.01); *C07C 17/37* (2013.01); *C07C 21/18* (2013.01)

(58) Field of Classification Search
CPC .............................. C07C 17/206; C07C 17/37
See application file for complete search history.

(56) References Cited

U.S. PATENT DOCUMENTS

| | | | |
|---|---|---|---|
| 3,081,358 A | 3/1963 | Agahigian et al. | |
| 4,814,522 A | 3/1989 | Weigert | |
| 5,895,825 A * | 4/1999 | Elsheikh | C07C 17/087 570/164 |
| 10,118,879 B1 * | 11/2018 | Jungong | C07C 17/383 |
| 2013/0150633 A1 * | 6/2013 | Zhai | C07C 17/10 570/154 |
| 2015/0321979 A1 * | 11/2015 | Yang | C07C 17/206 570/151 |
| 2017/0210686 A1 * | 7/2017 | Pigamo | B01J 12/007 |
| 2018/0214855 A1 * | 8/2018 | Ricou | C07C 17/206 |

FOREIGN PATENT DOCUMENTS

| | | |
|---|---|---|
| CN | 105727929 A | 7/2016 |
| JP | 2015120669 A | 7/2015 |

OTHER PUBLICATIONS

Nakamura, M. et al. Patent No. JP2015120669, Published Jul. 2, 2015, pp. 1-20; English translation attached herein (Year: 2015).*

* cited by examiner

*Primary Examiner* — Medhanit W Bahta
(74) *Attorney, Agent, or Firm* — Faegre Baker Daniels LLP

(57) ABSTRACT

A method for producing 1,3,3,3-tetrafluoropropene (HFO-1234ze, or 1234ze) from 1-chloro-3,3,3-trifluoropropene (HCFO-1233zd, or 1233zd). In one embodiment, HFO-1233zd is subjected to a disproportionation reaction in the presence of a catalyst at an elevated temperature to produce HFO-1234ze as well as 3,3-dichloro-1,1-difluoropropene (HCFO-1232zc). The catalyst may be at least one of a chromium oxyfluoride catalyst, a chromium oxide catalyst, or a metal fluoride catalyst. The reaction may be conducted in the vapor phase at a temperature between 100° C. and 450° C. Advantageously, in the present method, substantially no hydrogen fluoride (HF) is used as a reactant, and substantially no HF is produced as a product.

15 Claims, No Drawings

METHOD FOR PRODUCING 1,3,3,3-TETRAFLUOROPROPENE (HFO-1234ZE) FROM 1-CHLORO-3,3,3-TRIFLUOROPOPENE (HCFO-1233ZD)

CROSS REFERENCE TO RELATED APPLICATIONS

This application claims the benefit under Title 35, U.S.C. § 119(e) of U.S. Provisional Patent Application Ser. No. 62/589,824, entitled METHOD FOR PRODUCING 1,3,3,3-TETRAFLUOROPROPENE (HFO-1234ze) FROM 1-CHLORO-3,3,3-TRIFLUOROPROPENE (HCFO-1233zd), filed on Nov. 22, 2017, the entire disclosure of which is expressly incorporated by reference herein.

BACKGROUND

1. Field of the Disclosure

The present disclosure relates to a method for producing 1,3,3,3-tetrafluoropropene (HFO-1234ze, or 1234ze) from 1-chloro-3,3,3-trifluoropropene (HCFO-1233zd, or 1233zd).

2. Description of the Related Art

HFO-1234ze is a new low global warming potential (LGWP) and zero ozone depleting potential (ODP) hydrofluoroolefin (HFO) that is an energy-efficient alternative to traditional refrigerants used for applications in large stationary and commercial refrigeration, and in aerosol propellants and thermal insulating foams.

Most known production processes for producing HFO-1234ze involve utilization and/or generation of hydrofluoric acid (HF). For example, in a typical process, an appropriate chlorinated precursor is fluorinated with hydrofluoric acid (HF) to form an intermediate, followed by subsequent dehydrohalogenation of the intermediate to form HFO-1234ze, which also results in the formation of hydrochloric acid (HCl) or hydrofluoric acid (HF). The dehydrohalogenation of hydrochlorofluorocarbons (HCFCs) is generally endothermic, and is thermodynamically favored at high reaction temperatures. However, the formation of HF and/or HCl at high temperatures creates a corrosive mixture, such that separation of HF and/or HCl from reaction products and/or subsequent recycle or discharge of HF and/or HCl, requires corrosion-proof materials and poses potential sources of hazard and pollution.

Therefore, a process for the industrial production of HFO-1234ze that minimizes the use and production of HF and/or HCl would be desirable.

The disproportionation of alkenes to produce other alkenes has been referenced in the literature. For example, U.S. Pat. No. 3,081,358 discloses disproportionation of chloropentafluoropropenes in the presence of aluminum trifluoride (AlF$_3$) catalyst at temperatures from 300° C. to 450° C. to make one or both of hexafluoropropene or a 1,1-dichlorotetrafluoropropane. In another example, U.S. Pat. No. 4,814,522 discloses catalytic transhalogenation of perhaloolefins by reacting two perhaloolefins in the presence of chromium oxide or aluminum oxide, either alone or in combination with one or more additional metals. In the transhalogenation reaction, the catalyst is activated prior to use by heating the catalyst at a relatively high temperature between 300° C. and 400° C. in the presence of a suitable fluoroolefin. Examples of fluoroolefins used to activate the catalyst included tetrafluoroethylene, chlorotrifluoroethene, 1,1-dichloro-2,2-difluoroethane, hexafluoropropene, perfluoro-1-butene, and perfluoro-2-butene.

CN 105727929 A discloses the use of a quad-metallic catalyst for the gas phase fluorination of HCFO-1233zd at a temperature of 390° C. to form HFO-1234ze. JP 2015-120669 A discloses the concurrent reaction of HCFO-1233zd and another fluorocarbon (saturated or unsaturated) at a content ratio from 1:1 to 5:1 and in the presence of a metal catalyst to form HFO-1234ze and, specifically, the reaction of HCFO-1233zd and vinylidene fluoride in the presence of activated alumina to form HFO-1234ze.

SUMMARY

The present disclosure provides a method for producing 1,3,3,3-tetrafluoropropene (HFO-1234ze, or 1234ze) from 1-chloro-3,3,3-trifluororpropene (HCFO-1233zd, or 1233zd). In one embodiment, HFO-1233zd is subjected to a disproportionation reaction in the presence of a catalyst at an elevated temperature to produce HFO-1234ze as well as 3,3-dichloro-1,1-difluoropropene (HCFO-1232zc). The catalyst may be at least one of a chromium oxyfluoride catalyst, a chromium oxide catalyst, or a metal fluoride catalyst. The reaction may be conducted in the vapor phase at a temperature between 100° C. and 450° C. Advantageously, in the present method, substantially no hydrogen fluoride (HF) is used as a reactant, and substantially no HF is produced as a product.

In one form thereof, the present disclosure provides a method for producing 1,3,3,3-tetrafluoropropene (HFO-1234ze), including the steps of: providing a reactant composition including 1-chloro-3,3,3-trifluoropropene (HCFO-1233zd); and reacting the reactant composition in the presence of at least one catalyst selected from the group consisting of chromium oxyfluoride, chromium oxide, metal fluoride, and combinations thereof at catalyst in the vapor phase at an elevated temperature to produce a product composition including HFO-1234ze.

The reactant composition may include only HCFO-1233zd as a single reactant, the HCFO-1233zd having a purity of greater than 95 area % as determined by gas chromatography (GC). The product composition may also include 3,3-dichloro-1,1-difluoropropene (HCFO-1232zc).

The catalyst may be selected from the group consisting of amorphous chromium oxyfluoride, crystalline chromium oxyfluoride, and combinations of the foregoing.

The reactant composition may include less than 0.5 wt. % hydrogen fluoride (HF). The product composition may include less than 0.1 wt. % hydrogen fluoride (HF). The elevated temperature may be between 100° C. and 450° C.

In another form thereof, the present disclosure provides a method for producing 1,3,3,3-tetrafluoropropene (HFO-1234ze), including the steps of: providing a reactant composition including 1-chloro-3,3,3-trifluoropropene (HCFO-1233zd); and reacting the reactant composition in the presence of a chromium oxyfluoride catalyst in the vapor phase at a temperature between 100° C. and 450° C. to produce a product composition including HFO-1234ze, the product composition additionally including 3,3-dichloro-1,1-difluoropropene (HCFO-1232zc).

The reactant composition may include only HCFO-1233zd as a single reactant, the HCFO-1233zd having a purity of greater than 95 area % as determined by gas chromatography (GC).

The reactant composition may include less than 0.5 wt. % hydrogen fluoride (HF). The product composition may include less than 0.1 wt. % hydrogen fluoride (HF).

In a further form thereof, the present disclosure provides a method for producing 1,3,3,3-tetrafluoropropene (HFO-1234ze), including the steps of: providing a reactant composition including (Z)1-chloro-3,3,3-trifluoropropene (HCFO-1233zd(Z)); isomerizing the reactant composition in the presence of a chromium oxyfluoride catalyst in the vapor phase at a temperature between 100° C. and 450° C. to produce a first product composition including (E)1-chloro-3,3,3-trifluoropropene (HCFO-1233zd(E)); and reacting the first product composition in the presence of a chromium oxyfluoride catalyst in the vapor phase at a temperature between 100° C. and 450° C. to produce a second product composition including HFO-1234ze.

The second product composition may also include 3,3-dichloro-1,1-difluoropropene (HCFO-1232zc). The reactant composition may include less than 0.5 wt. % hydrogen fluoride (HF), and each of the first and second product compositions may include less than 0.1 wt. % hydrogen fluoride (HF).

DETAILED DESCRIPTION

The present disclosure provides a method for producing 1,3,3,3-tetrafluoropropene (HFO-1234ze, or 1234ze) from 1-chloro-3,3,3-trifluoropropene (HCFO-1233zd, or 1233zd). In one embodiment, HFO-1233zd is subjected to a disproportionation reaction in the presence of a catalyst at an elevated temperature to produce HFO-1234ze as well as 3,3-dichloro-1,1-difluoropropene (HCFO-1232zc). The catalyst may be at least one of a chromium oxyfluoride catalyst, a chromium oxide catalyst, or a metal fluoride catalyst. The reaction may be conducted in the vapor phase at a temperature between 100° C. and 450° C. Advantageously, in the present method, substantially no hydrogen fluoride (HF) is used as a reactant, and substantially no HF is produced as a product.

In the present disclosure, unless otherwise noted, the term "HCFO-1233zd" collectively refers to both the -trans and -cis isomers of HCFO-1233zd and, in this connection, the term "HCFO-1233zd(E/Z)" may also be used. Similarly, unless otherwise noted, the term "HCFO-1234ze" collectively refers to both the -trans and -cis isomers of HCFO-1234ze and, in this connection, the term "HCFO-1234ze(E/Z)" may also be used. Otherwise, single isomers will be referred to herein as HCFO-1233zd(E), HCFO-1233zd(Z), HCFO-1234ze(E), and HCFO-1234ze(Z).

The general reaction embodied by the present disclosure is set forth below as Reaction Scheme (1):

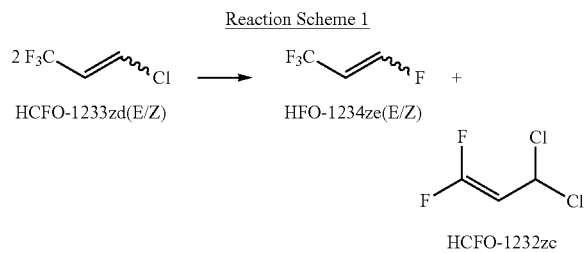

Reaction Scheme 1

The foregoing reaction is a disproportionation reaction, in which a single reactant, HCFO-1233zd(E/Z), is reacted to form both HFO-1234ze(E/Z) (a low oxidation state product) and HCFO-1232zc (a high oxidation state product) as products.

The reaction composition or feed stream includes HCFO-1233zd. In one embodiment, substantially pure HCFO-1233zd may be fed into a reactor. The purity of the HCFO-1233zd reactant composition may be greater than 90%, 95%, 97% or 99%, or even greater than 99.9%, expressed as area % as determined by gas chromatography (GC). In this connection, the reactant stream may include only a single reactant compound or a blend of the (E) and (Z) isomers of the single reactant compound, namely, HCFO-1233zd, with only trace impurities. In one embodiment, the reactant composition is highly pure HCFO-1233zd(E) of the foregoing purity, with substantially no HCFO-1233zd(Z) present in the reactant composition. In another embodiment, the reactant composition is highly pure HCFO-1233zd(Z) of the foregoing purity, with substantially no HCFO-1233zd(E) present in the reactant composition. In a further embodiment, the reactant stream is a blend of HCFO-1233zd(E) and HCFO-1233zd(Z) of the foregoing purity.

Therefore, the HCFO-1233zd reaction composition may include substantially only HCFO-1233zd, and any impurities, i.e., elements or compounds other than HCFO-1233zd, if present, are present in an amount of less than 10 wt. %, less than 5 wt. %, less than 3 wt. %, less than 1 wt. %, or less than 0.1 wt. %, based on the total weight of the reaction composition.

The reaction is carried out in the reactor in the presence of at least one catalyst. In particular, in the reactor the HCFO-1233zd is vaporized and reacted in the vapor phase in the presence of the catalyst which, as described below, may be a heterogeneous, solid catalyst. In one embodiment, the HCFO-1233zd reactant in a vapor phase may be passed over a heated column of the catalyst in a stainless steel tube reactor at elevated temperature.

The catalyst may be unsupported and in the form of pellets of various shapes, as well as beads, spheres, or sieves, for example. Alternatively, the catalyst may be supported on carbon, such as activated carbon in the form of pellets of various shapes, as well as beads, spheres, or sieves, for example. In other embodiments, the catalyst may be supported on alumina and/or silica in the any of the foregoing forms.

In one embodiment, the catalyst is a chromium oxyfluoride catalyst, such as amorphous chromium oxyfluoride ($Cr_xO_yF_z$, where x may be 1 or 2, y may be 1 or 2, and z may be 1, 2, or 4), crystalline chromium oxyfluoride ($Cr_xO_yF_z$, where x may be 1 or 2, y may be 1 or 2, and z may be 1, 2, or 4), or a combination of the foregoing.

In another embodiment, the catalyst may be a chromium oxide catalyst, such as fresh amorphous chromium oxide ($Cr_2O_3$) pretreated with HF, fresh crystalline chromium oxide ($Cr_2O_3$) pretreated with HF, amorphous chromium oxyfluoride, and crystalline chromium oxyfluoride, or any combination of the foregoing. The chromium oxide catalysts may be used unsupported or supported, as described above.

In a further embodiment, the catalyst may be a metal fluoride catalyst such as chromium trifluoride ($CrF_3$) or aluminum trifluoride ($AlF_3$). The metal fluorides may be used unsupported, or supported on activated carbon, alumina, or chromium oxides, for example.

Advantageously, in the present reaction, no prior activation of the catalyst is needed. In other words, the catalyst may be used "neat" in a manner in which the catalyst is added to the reactor, either on a support or without a support, wherein the catalyst is active in the presence of the reactant at the reaction temperatures disclosed herein.

The amount of catalyst used may vary, but generally the contact time between the reactant stream and the catalyst may be as little as 0.2 second, 10 seconds, or 50 seconds, or as great as 100 seconds, 125 seconds, or 150 seconds, or within any range defined between any pair of the foregoing values, such as from 0.2 second to 150 seconds, from 10 seconds to 125 seconds, or from 50 seconds to 100 seconds, for example.

Suitable reaction temperatures in the reactor may be as little as 100° C., 125° C., 150° C., 175° C., or as great as 225° C., 250° C., 275° C., 300° C., 400° C., or 450° C., or within any range defined between any pair of the foregoing values, such as from 100° C. to 450° C., 100° C. to 400° C., 100° C. to 300° C., from 125° C. to 275° C., from 150° C. to 250° C., or from 175° C. to 225° C., for example.

Suitable reaction pressures in reactor may be as little as 0, psig, 10 psig, or 20 psig, or as great as 50 psig, 75 psig, or 100 psig, or within any range defined between any pair of the foregoing values, such as from 0 psig to 100 psig, from 10 psig to 75 psig, or from 20 psig to 50 psig, for example. In one embodiment, the reaction pressure in the reactor is about 50 psig.

Advantageously, the present reaction may neither use nor generate hydrogen fluoride (HF). In particular, the reactant stream entering the reactor may include less than 1.0 wt. %, less than 0.5 wt. %, or less than 0.1 wt. % HF, and the product stream exiting the reactor may also include less than 1.0 wt. %, less than 0.5 wt. %, or less than 0.1 wt. % HF. Additionally, the present reaction may neither use nor generate hydrogen chloride (HCl). In particular, the reactant stream entering the reactor may include less than 1.0 wt. %, less than 0.5 wt. %, or less than 0.1 wt. % HCl, and the product stream exiting the reactor may also include less than 1.0 wt. %, less than 0.5 wt. %, or less than 0.1 wt. % HCl.

The present inventors have found that in the present reaction, HCFO-1233zd(E) is thermodynamically more stable relative to HCFO-1233zd(Z) during the reaction and in the presence of the catalyst. By contrast, HCFO-1233zd(Z) is more susceptible to isomerization, and may also be converted to HCFO-1233zd(E), which results in a lower selectivity to HFO-1234ze and HCFO-1232zc when HCFO-1233zd(Z) is present in the reactant feed stream. In addition, the HCFO-1232zc itself may also be sensitive to isomerization and may be potentially converted 1,3-dichloro-3,3-difluoropropene (HCFO-1232zd, or 1232zd).

Following the disproportionation reaction, the HFO-1234ze product is separated from unreacted HCFO-1233zd, the HCFO-1232zc co-product, and any other by-products by conventional distillation techniques. Unreacted HCFO-1233zd may be recycled back to the reactor. Similarly, the HCFO-1232zc and any of its isomers which are formed as products may be separated from unreacted HCFO-1233zd, the HCFO-1234ze co-product, and any other by-products by conventional distillation techniques and thereafter, may be concentrated for use as precursors for other value-added products or as monomers for production of polymers.

In an integrated, multi-reactor process, because HCFO-1233zd(Z) is more susceptible to isomerization than HCFO-1233zd(E), in a first step, HCFO-1233zd(Z) may be isomerized in the vapor phase in a first reactor in the presence of a catalyst and under the conditions set forth above to form HCFO-1233zd(E). Thereafter, in a second step, the HCFO-1233zd(E) product from the first reactor may be supplied to a second reactor and, in the presence of a catalyst and under the conditions set forth above, undergo the vapor phase disproportionation reaction described herein to form HFO-1234ze and HCFO-1232zc. The resulting HFO-1234ze product, and attendant by-products, may be separated by conventional distillation techniques.

In the present process, when HCFO-1233zd(E) is the sole reactant, with substantially no HCFO-1233zd(Z) present as a reactant, conversion of HCFO-1233zd(E) may be higher than 5%, higher than 7%, higher than 10%, up to 12%, for example. When HCFO-1233zd(Z) is the sole reactant, with substantially no HCFO-1233zd(E) present as a reactant, conversion of HCFO-1233zd(Z) may be higher than 90%, higher than 91%, higher than 93%, up to 95%, for example.

Also, in the present process, when HCFO-1233zd(E) is the sole reactant, with substantially no HCFO-1233zd(Z) present as a reactant, of the total products formed, the selectivity to HCFO-1234ze may be higher than 6%, higher than 7%, or higher than 10%, up to 14%, the selectivity to HCFO-1233zd(Z) may be higher than 75%, higher than 85%, or higher than 90%, up to 98%, and the selectivity to HCFO-1232zc may be higher than 0.5%, higher than 1%, or higher than 1.5%, up to 2%.

When HCFO-1233zd(Z) is the sole reactant, with substantially no HCFO-1233zd(E) present as a reactant, of the total products formed, the selectivity to HCFO-1234ze may be higher than 0.5%, higher than 1%, or higher than 1.5%, up to 2%, the selectivity to HCFO-1233zd(E) may be higher than 85%, higher than 90%, or higher than 95%, up to 98%, and the selectivity to HCFO-1232zc may be higher than 0.1%, higher than 0.2%, or higher than 0.3%, up to 0.5%.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

Example 1

Disproportionation of HCFO-1233zd(E)

A feed stream consisting of HCFO-1233zd(E) was vaporized and reacted in the vapor phase over chromium oxyfluoride catalyst to produce HFO-1234ze. Specifically, the feed stream consisting of >99.90 GC area % HCFO-1233zd(E) was vaporized and fed to a 1 inch (2.54 cm) reactor containing 0.28 L of amorphous chromium oxyfluoride catalyst pellets, at a rate of 0.6 lb/hr (272 g/hr) and reactor pressure of 50 psig. The reaction temperature was varied between 100 and 300° C. Table 1 below shows average conversions of HCFO-1233zd(E), and average selectivity to HFO-1234ze and by-products, as a function of temperature using chromium oxyfluoride catalyst.

TABLE 1

Average conversion of HCFO-1233zd(E) and average selectivity to HFO-1234ze and by-products using chromium oxyfluoride catalyst

| Temperature, | Average Conversion (%) | Average Selectivity (%) | | | |
|---|---|---|---|---|---|
| ° C. | 1233zd(E) | 1234ze(E/Z) | 1233zd(Z) | 1232zc | others |
| 150 | 5.57 | 1.58 | 97.20 | 0.47 | 0.74 |
| 200 | 7.98 | 6.00 | 91.83 | 1.64 | 0.54 |
| 225 | 9.17 | 7.99 | 88.82 | 1.73 | 1.46 |

TABLE 1-continued

Average conversion of HCFO-1233zd(E) and average selectivity to
HFO-1234ze and by-products using chromium oxyfluoride catalyst

| Temperature, °C. | Average Conversion (%) | Average Selectivity (%) | | | |
|---|---|---|---|---|---|
| | 1233zd(E) | 1234ze(E/Z) | 1233zd(Z) | 1232zc | others |
| 250 | 9.71 | 8.90 | 87.59 | 2.10 | 1.41 |
| 300 | 12.11 | 13.65 | 81.14 | 1.83 | 3.38 |

Feed composition: >99.9% 1233zd(E); pressure 50 psig; chromium oxyfluoride catalyst; amount loaded 410 g; flow rate 0.6 lb/hr (272 g/hr); reactor dimensions: 1" ID × 31" L (2.54 cm ID × 78.7 cm L). Each temperature was run for at least 20 hours.

Example 2

Disproportionation of HCFO-1233zd(E)

A feed stream consisting of HCFO-1233zd(E) was vaporized and reacted in the vapor phase over chromium oxyfluoride catalyst to produce HFO-1234ze. Specifically, the feed stream consisting of >99.90 GC area % HCFO-1233zd (E) was vaporized and fed to a 1 inch (2.54 cm) reactor containing 0.28 L of amorphous chromium oxyfluoride catalyst pellets, at a rate of 0.6 lb/hr (272 g/hr) and reactor pressure of 50 psig. The reaction temperature was maintained between 220 and 230° C., specifically at around 225° C., while the feed flow rate was varied from 0.6-4.8 lb/hr (272 g-2.18 kg)/hr. Table 2 below shows average conversions of HCFO-1233zd(E), and average selectivity to HFO-1234ze and by-products, as a function of catalyst contact time using chromium oxyfluoride catalyst.

TABLE 2

Average conversion of HCFO-1233zd(E) and average selectivity to HFO-1234ze
and by-products using chromium oxyfluoride catalyst, at various contact times

| Flow Rate (lb/hr) | Contact time (sec) | Conversion (%) | Selectivity (%) | | | |
|---|---|---|---|---|---|---|
| | | 1233zd(E) | 1234ze(E/Z) | 1233zd(Z) | 1232zc | others |
| 0.6 | 43.13 | 9.17 | 7.99 | 87.98 | 1.67 | 2.36 |
| 1.2 | 21.56 | 9.35 | 8.05 | 88.63 | 2.06 | 1.26 |
| 2.4 | 10.78 | 9.29 | 6.62 | 90.69 | 2.16 | 0.53 |
| 4.8 | 5.38 | 8.17 | 4.36 | 93.5 | 1.67 | 0.47 |

Feed composition: 100% 1233zd(E);
temperature 225° C.;
pressure 50 psig;
catalyst: chromium oxyfluoride;
amount loaded 410 g;
reactor dimensions: 1" ID × 31" L (2.54 cm ID × 78.7 cm L).

Example 3

Disproportionation of HCFO-1233zd(Z)

A feed stream consisting of HCFO-1233zd(Z) was vaporized and reacted in the vapor phase over chromium oxyfluoride catalyst to produce HFO-1234ze. Specifically, the feed stream consisting of >99.90 GC area % HCFO-1233zd (Z) was vaporized and fed to a 1 inch (2.54 cm) reactor containing 0.28 L of amorphous chromium oxyfluoride catalyst pellets, at a rate of 0.6 lb/hr (272 g/hr) and reactor pressure of 50 psig. The reaction temperature was maintained between 220 and 230° C. Table 3 below shows average conversions of HCFO-1233zd(Z), and average selectivity to HFO-1234ze and by-products, as a function of time using chromium oxyfluoride catalyst.

TABLE 3

Average conversion of HCFO-1233zd(Z) and average selectivity to
HFO-1234ze and byproducts using chromium oxyfluoride catalyst

| Time, h | Average Conversion (%) | Average Selectivity (%) | | | |
|---|---|---|---|---|---|
| | 1233zd(Z) | 1234ze(E/Z) | 1233zd(E) | 1232zc | others |
| 8 | 91.79 | 1.07 | 98.63 | 0.15 | 0.15 |
| 16 | 91.24 | 0.74 | 98.92 | 0.18 | 0.16 |
| 24 | 91.84 | 0.71 | 98.90 | 0.18 | 0.21 |
| 32 | 91.75 | 0.68 | 98.97 | 0.18 | 0.16 |
| 40 | 91.91 | 0.66 | 98.98 | 0.18 | 0.18 |

Feed composition: >99.5% 1233zd(Z); pressure 50 psig; chromium oxyfluoride; amount loaded 410 g; flow rate 0.6 lb/hr (272 g/hr): reactor dimensions: 1" ID × 31" L (2.54 cm ID × 78.7 cm L).

The low selectivity to HCFO-1234ze was caused by the susceptibility of HCFO-1233zd(Z) to undergo isomerization to form HCFO-1233zd(E).

While this disclosure has been described as having a preferred design, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method for producing 1,3,3,3-tetrafluoropropene (HFO-1234ze), comprising the steps of:

providing a reactant composition including 1-chloro-3,3,3-trifluoropropene (HCFO-1233zd), wherein the reactant composition includes only HCFO-1233zd as a single reactant, the HCFO-1233zd having a purity of greater than 90 area % as determined by gas chromatography (GC); and reacting the reactant composition in the presence of at least one catalyst selected from the group consisting of chromium oxyfluoride, chromium oxide, metal fluoride, and combinations thereof at catalyst in the vapor phase at an elevated temperature to produce a product composition including HFO-1234ze.

2. The method of claim 1, the HCFO-1233zd has a purity of greater than 95 area % as determined by gas chromatography (GC).

3. The method of claim 1, wherein the product composition also includes 3,3-dichloro-1,1-difluoropropene (HCFO-1232zc).

4. The method of claim 1, wherein the catalyst is chromium oxyfluoride, the chromium oxyfluoride selected from the group consisting of amorphous chromium oxyfluoride, crystalline chromium oxyfluoride, and combinations of the foregoing.

5. The method of claim 1, wherein the reactant composition includes less than 0.5 wt. % hydrogen fluoride (HF).

6. The method of claim 1, wherein the product composition includes less than 0.1 wt. % hydrogen fluoride (HF).

7. The method of claim 1, wherein the elevated temperature is between 100° C. and 450° C.

8. A method for producing 1,3,3,3-tetrafluoropropene (HFO-1234ze), comprising the steps of:
   providing a reactant composition including 1-chloro-3,3,3-trifluoropropene (HCFO-1233zd), wherein the reactant composition includes no other source of fluorine; and
   reacting the reactant composition in the presence of a chromium oxyfluoride catalyst in the vapor phase at a temperature between 100° C. and 450° C. to produce a product composition including HFO-1234ze, the product composition additionally including 3,3-dichloro-1,1-difluoropropene (HCFO-1232zc).

9. The method of claim 8, wherein the HCFO-1233zd has a purity of greater than 90 area % as determined by gas chromatography (GC).

10. The method of claim 8, wherein the reactant composition includes less than 0.5 wt. % hydrogen fluoride (HF).

11. The method of claim 8, wherein the product composition includes less than 0.1 wt. % hydrogen fluoride (HF).

12. A method for producing 1,3,3,3-tetrafluoropropene (HFO-1234ze), comprising the steps of:
    providing a reactant composition including (Z)1-chloro-3,3,3-trifluoropropene (HCFO-1233zd(Z)) to a first reactor;
    isomerizing the reactant composition in the first reactor in the presence of a chromium oxyfluoride catalyst in the vapor phase at a temperature between 100° C. and 450° C. to produce a first product composition including (E)1-chloro-3,3,3-trifluoropropene (HCFO-1233zd(E));
    providing the first product composition to a second reactor; and
    reacting the first product composition in the second reactor in the presence of a chromium oxyfluoride catalyst in the vapor phase at a temperature between 100° C. and 450° C. to produce a second product composition including HFO-1234ze.

13. The method of claim 12, wherein the second product composition also includes 3,3-dichloro-1,1-difluoropropene (HCFO-1232zc).

14. The method of claim 12, wherein the reactant composition includes less than 0.5 wt. % hydrogen fluoride (HF).

15. The method of claim 12, wherein each of the first and second product compositions include less than 0.1 wt. % hydrogen fluoride (HF).

* * * * *